US008003826B2

(12) United States Patent
Lettmann et al.

(10) Patent No.: US 8,003,826 B2
(45) Date of Patent: Aug. 23, 2011

(54) METHOD FOR PRODUCTION OF TRIMETHYLHEXAMETHYLENEDIAMINE

(75) Inventors: Christian Lettmann, Coesfeld (DE); Gerda Grund, Coesfeld (DE); Juergen Lippe, Gelsenkirchen (DE); Cord Knoop, Haltern am See (DE)

(73) Assignee: Evonik Degussa GmbH, Essen (DE)

( * ) Notice: Subject to any disclaimer, the term of this patent is extended or adjusted under 35 U.S.C. 154(b) by 11 days.

(21) Appl. No.: 12/529,587

(22) PCT Filed: Jan. 30, 2008

(86) PCT No.: PCT/EP2008/051101
§ 371 (c)(1),
(2), (4) Date: Sep. 2, 2009

(87) PCT Pub. No.: WO2008/107236
PCT Pub. Date: Sep. 12, 2008

(65) Prior Publication Data
US 2010/0094058 A1    Apr. 15, 2010

(30) Foreign Application Priority Data
Mar. 7, 2007   (DE) .................. 10 2007 011 484

(51) Int. Cl.
*C07C 209/48* (2006.01)
(52) U.S. Cl. ....................... 564/491; 564/492

(58) Field of Classification Search ............. 564/491, 564/492
See application file for complete search history.

(56) References Cited

U.S. PATENT DOCUMENTS

| 3,418,375 | A | * | 12/1968 | Schmitt et al. ............. 564/491 |
| 3,862,911 | A | | 1/1975 | Chabert |
| 4,987,263 | A | * | 1/1991 | Cordier ..................... 564/491 |
| 5,254,738 | A | * | 10/1993 | Koehler et al. ............. 564/491 |
| 5,679,860 | A | | 10/1997 | Haas et al. |
| 6,198,002 | B1 | * | 3/2001 | Eller et al. ................. 564/491 |
| 2009/0018366 | A1 | | 1/2009 | Berweiler et al. |
| 2009/0048466 | A1 | | 2/2009 | Lettmann et al. |

FOREIGN PATENT DOCUMENTS

| DE | 195 40 191 | | 11/1996 |
| WO | 2005 039766 | | 5/2005 |
| WO | WO 2007/028411 | * | 3/2007 |

OTHER PUBLICATIONS

U.S. Appl. No. 12/525,841, filed Aug. 5, 2009, Lettmann, et al.

* cited by examiner

*Primary Examiner* — Brian J Davis
(74) *Attorney, Agent, or Firm* — Oblon, Spivak, McClelland, Maier & Neustadt, L.L.P.

(57) ABSTRACT

The invention relates to an improved process for preparing trimethylhexamethylenediamine, hereinafter referred to as TMD for short, by hydrogenation of trimethylhexamethylenedinitrile, hereinafter referred to as TMN for short, in the presence of a shaped hydrogenation catalyst of the Raney type.

24 Claims, No Drawings

METHOD FOR PRODUCTION OF TRIMETHYLHEXAMETHYLENEDIAMINE

The invention relates to an improved process for preparing trimethylhexamethylenediamine, hereinafter referred to as TMD for short, by hydrogenation of trimethylhexamethylenedinitrile, hereinafter referred to as TMN for short, in the presence of a shaped hydrogenation catalyst of the Raney type.

TMD is used as epoxy resin hardener, as amine component in polyamides and as starting component for trimethylhexamethylenediisocyanate which is in turn a starting compound for polyurethane systems. TMD is preferably prepared industrially by hydrogenation of TMN:

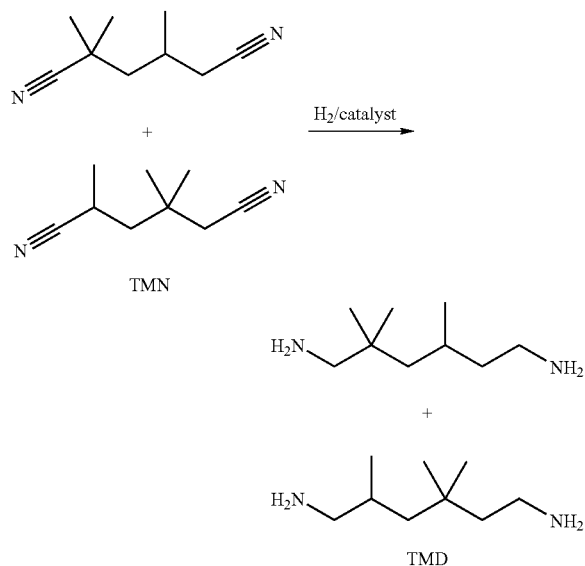

Due to the production process for TMN, a mixture of 2,4,4- and 2,2,4-trimethylhexamethylenedinitrile (about 60:40) is used in the hydrogenation. Hydrogenation gives a corresponding isomer mixture of 2,4,4- and 2,2,4-trimethylhexamethylenediamine.

Significant secondary reactions are the formation of trimethylcyclopentyldiamine and trimethylazacyclo-heptane.

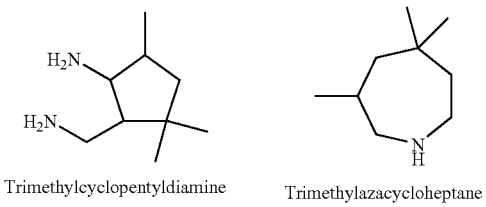

Trimethylcyclopentyldiamine     Trimethylazacycloheptane

Compared to the related conversion of adiponitrile into hexamethylenediamine, the hydrogenation of TMN to TMD is significantly more demanding, since ring formation leading to the by-products described is promoted by the methyl substituents. This is, firstly, attributable to more difficult hydrogenation of the nitrile groups due to the steric hindrance caused by the methyl substituents, as a result of which the relative rate of by-product formation is increased. Secondly, the methyl substituents stabilize polar intermediates which, according to the mechanism of the Thorpe-Ziegler cyclization, occur in ring formation from dinitriles:

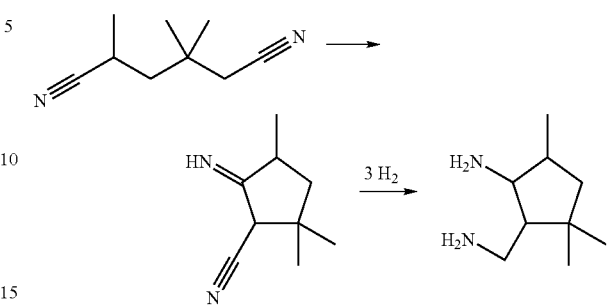

Thus, DE 15 18 345 states that when using a Raney nickel catalyst in the hydrogenation of adiponitrile, the target product hexamethylenediamine is obtained in yields of greater than 90%, while the reaction of TMN under identical conditions gives a TMD yield of only about 15%. Activated metal catalysts are known as Raney catalysts in chemical technology. They are predominantly used as powder catalysts in a large number of hydrogenation reactions. Raney catalysts are produced from an alloy of the catalytically active metal and an alloying component which is soluble in alkalis. Catalytically active components used are mainly nickel, cobalt, copper and iron. As leachable alloying constituent, use is made predominantly of aluminium, but zinc and silicon are also suitable. The Raney alloy is usually finely milled and the leachable component is subsequently completely or partially removed by leaching with alkalis, e.g. sodium hydroxide solution. Powder catalysts have the disadvantage that they can only be used in batch processes. For this reason, various processes which make it possible to produce activated fixed-bed metal catalysts have been described. Such fixed-bed catalysts of the Raney type are particularly useful for the industrial preparation of TMD since they make continuous operation of the process possible.

DE 43 45 265 and DE 43 35 360 describe shaped Raney catalysts based on Ni, Co, Cu and Fe which are suitable for the hydrogenation of organic compounds. The disadvantage of the catalysts is that metal powder has to be added as binder to the catalysts and the added metal powder is of relatively low catalytic activity compared to the Raney metal.

EP 880 996 describes the production of shaped Raney catalysts which are produced without addition of metallic binders and can be used for the hydrogenation of nitriles. To produce these catalysts, a metal-aluminium alloy in powder form is mixed with a high molecular weight polymer and, if desired, promoters and subsequently shaped to give shaped bodies, e.g. by extrusion. The shaped bodies are subsequently calcined at temperatures of up to 850° C. The heat treatment leads to controlled decomposition of the polymer and to formation of a fixed-bed catalyst having satisfactory mechanical stability. The catalyst is subsequently activated by leaching out the aluminium by means of sodium hydroxide solution. A disadvantage of this process is that a major part of the metal-aluminium alloy used remains unutilized since the leaching of the aluminium and thus activation of the catalyst occurs only in the outer shell of the shaped body. The core of the catalyst continues to comprise the metal-aluminium alloy used and is catalytically inactive, so that a considerable part of the relatively expensive alloys remains unutilized and serves only as support for the activated Raney metal layer.

Optimized utilization of the Raney metal alloy used is achieved when fixed-bed Raney catalysts in the form of hollow bodies as can be obtained according to the teachings of EP 1 068 900 are used. To produce the catalysts, a mixture of the desired alloy, an organic binder and if desired an inorganic binder are sprayed uniformly through a fluidized bed of polystyrene spheres, where it coats the spheres. The coated spheres are then calcined at temperatures in the range from 450 to 1000° C. in order to burn out the polystyrene and sinter the metal to make the hollow shape more stable. After calcination, the catalyst is activated by means of sodium hydroxide solution. The catalysts are suitable for the hydrogenation, dehydrogenation, hydration and isomerization of organic compounds. The particular advantage of this type of catalysts is that a large part of the alloy used is catalytically active after the activation and the activity of the catalyst based on the mass of alloy used is thus particularly high. The inventory of relatively expensive alloy can be minimized as a result.

A disadvantage of the catalysts described in EP 1 068 900 is the comparatively complicated production process. A particularly critical phase of the production process is the time between burning out of the polystyrene spheres and formation of a stable shell. In addition, the catalysts have, owing to their hollow body structure, a lower fracture strength than catalysts which have a solid core. Furthermore, the catalysts have a relatively low bulk density of only from 0.3 to 1.3 g/ml, which restricts their use in fixed-bed reactors through which liquid flows from the bottom upwards since the catalyst particles can easily be set into motion by the flowing medium, as a result of which deactivation by mechanical attrition is increased.

It is an object of the present invention to develop a process for preparing TMD from TMN, in which use is made of hydrogenation catalysts of the Raney type which contain very little metal alloy and equal or better TMD yields compared to previously known processes in which hydrogenation catalysts of the Raney type are used are nevertheless achieved.

It has now surprisingly been found that the object addressed can be achieved by use of the catalysts described in the document PCT/EP/2005/009656. This observation is surprising since it cannot necessarily be assumed that use of the catalysts described in PCT/EP/2005/009656 will give the required TMD yields in the specific case of the hydrogenation of TMN which is bulkier than adiponitrile to form TMD.

PCT/EP/2005/009656 describes fixed-bed Raney catalysts which can be obtained by application of a Raney alloy to a support such as silicon dioxide or aluminium oxide, in particular by spraying. The application of the alloy to the support, in particular by spraying, gives shaped bodies in which only the outer shell comprises the alloy while the inner core of the shaped body comprises the support material used. The use of the support material minimizes the specific use of relatively expensive alloys. Activation of the shaped bodies is carried out in a known manner by treatment with acid or alkali. The advantages of the catalysts described in PCT/EP/2005/009656 over the hollow bodies of EP 1 068 900, are the less complicated production and thus reduced production costs, a higher mechanical stability and a greater variability of the bulk density.

The invention provides a process for preparing trimethylhexamethylenediamine by aminative hydrogenation of mixtures containing trimethylhexamethylenedinitrile in the presence of at least ammonia and hydrogen, in which a shaped Raney-type hydrogenation catalyst produced by a production process comprising the following steps:
1) production of the catalyst precursor by application of a pulverulent alloy to a support material, with the alloy comprising at least one active metal and a second leachable alloy component selected from among aluminium, silicon and zinc,
2) optional drying and calcination of the shaped bodies obtained in step 1),
3) activation of the shaped bodies obtained in step 1) or 2) by means of acid and/or alkali,
4) optionally further modification of the catalyst which has been activated in step 3), e.g. by application of metals and/or metal salts and/or acids or bases and/or by treatment in a reducing or oxidizing atmosphere,
is used.

The catalysts to be used according to the invention can be obtained by the process described in PCT/EP/2005/009656.

The catalyst precursor is produced by applying one or more alloy powders to a support material. The supports can be a wide variety of materials, e.g. inorganic oxides such as alumina, silica, silica-alumina, magnesia, zinc oxide, titanium dioxide, zirconium dioxide and mixtures of these oxides. Other inorganic materials such as ceramics, shaped bodies made of metals, glass spheres, activated carbon, silicon carbide, calcium carbonate and barium sulphate are also suitable.

In a preferred embodiment of the invention, alloys based on cobalt/aluminium and/or nickel/aluminium, particularly preferably based on cobalt/nickel/aluminium, and supports based on alumina, silica and alumina-silica are used. It is advantageous for the support to have a very low pore volume and a relatively inert surface in order to prevent secondary reactions occurring on the support material.

The application of the alloy to the support is preferably effected by spraying a liquid suspension containing at least the alloy powder(s) and optionally one or more of the following components: inorganic binder (e.g. Ni, Co, Fe, Cu, other metal powders or inorganic powders), organic binders (e.g. polyvinyl alcohol), water, promoters, pore formers. The particle size of the pulverulent alloy is in the range from 1 to 200 µm. Application of the suspension to the support can be carried out, for example in a drum or a spray chamber. It is possible to carry this out at elevated temperature so that liquid introduced, e.g. water, is removed during this preparation step.

It may be necessary to pretreat the support in order to improve adhesion of the alloy to be applied. Processes in which the surface of the support is roughened or modified by, for example, acid treatment or pickling processes are useful. It may be advantageous to modify the surface properties of the support by preliminary application of a material which acts as a type of binder between support material and alloy. Binders which can be used are, for example, inorganic oxides such as aluminium oxide, titanium dioxide or metal powders.

The resulting catalyst precursors are optionally further dried and calcined in an additional process step, preferably at temperatures in the range from 100 to 1200° C., particularly preferably from 100 to 1000° C.

The catalysts used according to the invention can also consist of a plurality of layers. The catalyst precursors are then preferably dried between the individual coating steps, preferably at temperatures in the range from 60 to 150° C. The catalyst precursor is activated by leaching out the soluble alloying component, preferably by means of an aqueous mineral base such as sodium hydroxide. The activated catalyst is subsequently washed with water.

The mass ratio of leachable alloying component to active metal component in the alloy is preferably in the range from 20:80 to 80:20. The catalysts to be used according to the invention preferably comprise not only the leachable alloying components and the active metal components but also further doping elements or promoters selected from IIa, IIIb, IVb, Vb, VIb, VIIb, VIII, Ib, IIb, IIIa, IVa and Va, preferably from the group consisting of transition metal groups IIIb to VIIb and VIII, including the rare earths. Main group elements and their compounds, in particular those of main groups 1 and 2, are also suitable as promoters. The doping of Raney-type catalysts is described, for example, in the documents U.S. Pat. No. 4,153,578, DE 21 01 856, DE 21 00 373 or DE 20 53 799. Particularly preferred promoters are magnesium, chromium, manganese, iron, cobalt, vanadium, tantalum, titanium, cerium, tungsten, rhenium, platinum, palladium, ruthenium, nickel, copper, silver, gold and/or molybdenum. Very particular preference is given to magnesium, chromium and/or nickel. The promoters can be added as alloying constituents and/or at any point in time during the preparation, e.g. only after the activation step. The promoters can be added either in elemental form or in the form of their compounds. The proportion of promoters in the catalyst is up to 20% based on the total weight of the catalyst.

The bulk density of the catalysts can be set in a wide range from 0.8 to 3 g/ml and is particularly dependent on the bulk density of the support material and also on its proportion by mass in the catalyst, i.e. the ratio of support mass to total mass of the catalyst.

The process of the invention for preparing TMD can be carried out batchwise or continuously. The hydrogenation is preferably carried out continuously in fixed-bed reactors which can be operated in the downflow mode or upflow mode. Suitable types of reactor are, for example, shaft ovens, tray reactors or shell-and-tube reactors. It is also possible to connect a plurality of fixed-bed reactors in series for the hydrogenation, with each of the reactors being operated as desired in the downflow mode or upflow mode. The hydrogenation is usually carried out at temperatures in the range from 20 to 150° C., preferably from 40 to 130° C., at pressures of from 0.3 to 50 MPa, preferably from 5 to 30 MPa. To control the temperature profile in the reactor and in particular to limit the maximum temperature, various methods known to those skilled in the art are possible. Thus, for example, the reaction can be carried out completely without additional reactor cooling, with the reaction medium taking up all of the energy liberated and thereby conveying it convectively out of the reactor. Those suitable are, for example, tray reactors with intermediate cooling, the use of hydrogen circuits with gas cooling, recirculation of part of the cooled product (circulation reactor) and the use of external coolant circuits, especially in the case of shell-and-tube reactors.

The hydrogen required for the hydrogenation can be fed to the reactor either in excess, for example an amount of up to 10 000 molar equivalents, or only in such an amount that the hydrogen consumed by the reaction and the part of the hydrogen which leaves the reactor as a solution in the product stream is introduced. In continuous operation, the hydrogen can be conveyed in cocurrent or countercurrent.

In a preferred embodiment, the hydrogenation of TMN to TMD of the catalysts used according to the invention is carried out in liquid ammonia solvent. Per mole of TMN, from 1 to 500 mol, preferably from 5 to 200 mol, particularly preferably from 5 to 100 mol, of ammonia are used.

Although the hydrogenation of TMN to TMD in the presence of ammonia is preferably carried out without addition of further solvents, it can also be carried out in the presence of additional solvents. Suitable solvents include monohydric alcohols having from 1 to 4 carbon atoms, in particular methanol, and ethers, in particular THF, MTBE and dioxane. The significant advantage of the use of an additional solvent or of solvent mixtures is that the hydrogenation can be carried out at lower pressures than when ammonia is used as sole solvent.

The required volume of the catalysts to be used according to the invention is a function of the LHSV (liquid hourly space velocity) which has to be adhered to in order to ensure very complete hydrogenation of the TMN. The LHSV in turn depends on the operating pressure, the temperature, the concentration and the catalyst activity. The LHSV when using the preferred mixture of TMN, ammonia and hydrogen is usually in the range from 0.5 to 4 $m^3$ of TMN/ammonia mixture per $m^3$ of catalyst and hour, preferably from 1 to 3 $m^3/(m^3 \times h)$.

The reaction mixture leaving the hydrogenation reactor is worked up in a manner known per se. This work-up usually comprises removal of the ammonia, the solvent or mixtures of solvent and ammonia, if solvents are present, and isolation of the TMD. The ammonia which has been separated off and any further solvents which have been separated off are recirculated to the process either in their entirety or optionally after discharge of a substream.

Apart from the abovementioned constituents, the mixture to be fed to the hydrogenation reactor can additionally contain fractions which have higher or lower boiling points than TMD and are obtained in the work-up of the reaction mixture by distillation. Such fractions can contain not only residues of TMD but also by-products from which TMD is reformed under the reaction conditions. It is particularly advantageous to recirculate fractions containing incompletely reacted TMN or amino nitrile.

It is preferred but not absolutely necessary that the hydrogenation catalysts to be used according to the invention be firstly conditioned by means of ammonia before use in the hydrogenation. For this purpose, the catalysts are brought into contact with ammonia or with mixtures of ammonia and one or more solvents. Conditioning is preferably carried out after installation of the catalysts in the hydrogenation reactor, but it can also be carried out before installation of the catalysts. The conditioning is carried out using from 0.2 to 3 $m^3$, preferably from 0.5 to 2 $m^3$, of ammonia per $m^3$ of catalyst and hour. It is usually carried out at temperatures in the range from 20 to 150° C., preferably from 40 to 130° C. Particular preference is given to employing a temperature ramp according to which the catalyst is initially heated to a moderately elevated temperature, preferably in the range from 20 to 50° C., and then slowly heated to the reaction temperature which is desired later for the hydrogenation, preferably from 20 to 150° C. Conditioning is preferably carried out in the presence of hydrogen, with the partial pressure of the hydrogen used in the reactor being in the range from 0.1 to 30 MPa, preferably from 5 to 25 MPa, particularly preferably from 10 to 20 MPa. The time for which conditioning is carried out depends on the amount of ammonia used and is preferably in the range from 1 to 48 hours, particularly preferably from 12 to 24 hours.

Regardless of whether the process of the invention is carried out according to a preferred embodiment or not, one or more hydroxide bases can be added in the reaction of a mixture of TMN, ammonia, hydrogen and if desired solvent. The addition of hydroxide bases enables the yield of TMD to be increased by reducing by-product formation. Suitable hydroxide bases are, for example, alkali metal hydroxides or alkaline earth metal hydroxides. Particularly preferred hydroxide bases are quaternary ammonium hydroxides of the general formula $(R^1R^2R^3R^4N)OH$, where $R^1$ to $R^4$ can be identical or different and are each an aliphatic, cycloaliphatic or aromatic radical. Examples are tetramethylammonium, tetraethylammonium, tetra-n-propylammonium and tetra-n-butylammonium hydroxides. Suitable concentrations are from 0.01 to 100 mmol, preferably from 0.05 to 20 mmol, of a tetraalkylammonium hydroxide per mole of TMN.

It is also possible to use one or more cocatalysts in the process of the invention. Suitable cocatalysts are salts of cobalt, nickel, lanthanum, cerium or yttrium, preferably salts of cobalt and nickel.

EXAMPLES

Catalyst According to the Invention

A coating solution is prepared by suspending 776 g of a Co/Al/Cr/Ni alloy in 700 g of water containing magnesium nitrate and polyvinyl alcohol.

This suspension is then sprayed onto 1350 ml of glass spheres having an average diameter of from 1.5 to 2 mm. For this purpose, the glass spheres are firstly suspended in an upwards-directed stream of air and preheated to about 80° C. The suspension is subsequently sprayed on, with a temperature of about 90° C. being set during the spraying process in order to evaporate the water introduced.

After the glass spheres have been coated with the abovementioned solution, the spheres are dried further in upflowing air at a temperature of about 90° C. In a second step, 1350 ml of the dried, coated glass spheres are then coated with a further alloy solution.

A coating solution is prepared by suspending 675 g of a Co/Al/Cr/Ni alloy in 607 g of water containing 2% by weight of polyvinyl alcohol.

The suspension is then sprayed onto the precoated glass spheres under the same conditions as described above.

After the second coating step, the coated glass spheres are heated at 900° C. in a stream of air/nitrogen in order to burn out the polyvinyl alcohol and sinter the alloy particles together. The spheres are then activated by means of chromium, nickel and/or magnesium in a 20% strength by weight sodium hydroxide solution at 90° C. for 1.5 hours.

The activated spheres had a diameter of about 3.5 mm and a shell thickness of 800-900 μm.

Comparative Catalyst

A fixed-bed Raney cobalt catalyst in the form of a hollow sphere was produced according to the teachings of the documents EP 1 068 900 and EP 1 216 985. A coating solution is prepared by suspending 800 g of a Co/Al/Cr/Ni alloy in 1000 ml of water containing magnesium nitrate and polyvinyl alcohol.

This suspension is then sprayed onto 2000 ml of polystyrene spheres having an average diameter of about 2 mm while these spheres are suspended in an upwards-directed stream of air. For this purpose, the polystyrene spheres are firstly suspended in an upwards-directed stream of air and preheated to about 80° C. The suspension is subsequently sprayed on, with a temperature of about 90° C. being set during the spraying process in order to evaporate the water introduced.

After the polystyrene spheres have been coated with the abovementioned solution, the spheres are dried in upwards-flowing air at temperatures up to 90° C.

In a second step, 1000 ml of these dried, coated polystyrene spheres are coated further with an alloy solution. The solution for the second layer comprises 800 g of a Co/Al/Cr/Ni alloy which is suspended in 1000 ml of an aqueous solution of magnesium nitrate and polyvinyl alcohol.

The suspension is then sprayed onto the precoated polystyrene spheres under the same conditions as described above.

After the second coating step, the coated polystyrene spheres are heated at 900° C. in a stream of nitrogen/air in order to burn out the polystyrene and sinter the alloy particles together. The hollow spheres are then activated in a 20% strength by weight sodium hydroxide solution at 80° C. for 1.5 hours. The activated hollow spheres obtained have diameters in the region of 3 mm and a wall thickness of about 700 μm.

Hydrogenation of TMN Using the Catalyst According to the Invention and the Comparative Catalyst The experimental apparatus comprised three heatable fixed-bed reactors which were connected in series and were each filled with about 2 of the hydrogenation catalyst to be tested. The catalyst was conditioned by passing 3 kg of ammonia over the fixed beds at 100° C. During conditioning, a hydrogen partial pressure of about 100 bar was set. After 12 hours, conditioning was stopped. Directly after conditioning, 6 kg of a solution of 17% by weight of IPN in ammonia which had been heated to 50° C. were fed in. The flow through the hydrogenation reactor was from the top downwards (downflow mode). The pressure in the hydrogenation reactor was kept constant at 250 bar by introduction of hydrogen via a regulating valve. The temperature in the reactors was set by means of external heating so as to give a temperature profile which corresponded to the progress of the reaction in adiabatic operation. The composition of the end product was determined by means of gas chromatography.

A comparison of the composition of the products when using the catalysts according to the invention and the comparative catalyst is shown in Table 1. The TMN conversion was 100% in all experiments.

TABLE 1

| Composition of the end product (GC %) | When using the catalyst according to the invention | When using the comparative catalyst |
| --- | --- | --- |
| Total TMD | 96.3 | 95.7 |
| Trimethylcyclopentyl-diamine | 0.5 | 1.1 |
| Trimethylazacyclo-heptane | 2.6 | 3 |
| Unknowns | 0.6 | 0.2 |

The experiments show that the TMD yield when using the catalyst to be used according to the invention is higher than when using the comparative catalyst.

The invention claimed is:

1. A process for preparing trimethylhexamethylenediamine, comprising aminatively hydrogenating a mixture comprising trimethylhexamethylenedinitrile in the presence of at least ammonia and hydrogen, wherein said hydrogenating is carried out in the presence of a shaped Raney-type hydrogenation catalyst produced by a production process comprising:
   1) producing a catalyst precursor by application of a pulverulent alloy to a support material, wherein the alloy comprises at least one active metal and a second leachable alloy component selected from the group consisting of aluminium, silicon and zinc,
   2) optionally drying and calcinating the shaped body obtained in 1),
   3) activating the shaped body obtained in 1) or 2) by at least one of acid and alkali.

2. The process according to claim 1, wherein the active metal comprises at least one of metals of group VIII and Ib of the Periodic Table.

3. The process according to claim 1, wherein the active metal comprises at least one of cobalt, nickel, iron and copper.

4. The process according to claim 1, wherein
the alloy comprises at least one of cobalt/aluminium and nickel/aluminium.

5. The process according to claim 1, wherein
the pulverulent alloy comprises at least one of inorganic or organic binder, promoter, acid and base.

6. The process according to claim 1, wherein
the pulverulent alloy comprises a dopant metal.

7. The process according to claim 1, wherein the hydrogenating is carried out in the presence of a promoter or a dopant metal comprising at least one element selected from the group consisting of Groups IIa, IIIb, IVb, Vb, VIb, VIIb, VIII, Ib, IIb, IIIc, IVa and Va of the Periodic Table.

8. The process according to claim 1, wherein the hydrogenating is carried out in the presence of
a promoter compound comprising at least one element selected from the group consisting of magnesium, chromium, manganese, iron, cobalt, vanadium, tantalum, titanium, cerium, tungsten, rhenium, platinum, palladium, ruthenium, nickel, copper, silver, gold and molybdenum.

9. The process according to claim 1, wherein the support comprises at least one of
alumina, silica, silica-alumina, magnesia, zinc oxide, titanium dioxide, zirconium dioxide, a mixture of these oxides, a ceramic, a shaped body of metals, glass spheres, activated carbon, silicon carbide, calcium carbonate and barium sulphate.

10. The process according to claim 1, wherein
the support comprises aluminium, silica or alumina-silica.

11. The process according to claim 1, wherein during the producing
at least one of an inorganic binder and an organic powder is present and comprises a metal powder.

12. The process according to claim 1, wherein a polyvinyl alcohol is present during the producing.

13. The process according to claim 1, wherein the particle size of the pulverulent alloy is in the range from 1 to 200 μm.

14. The process according to claim 1, wherein the catalyst activated in 3) is modified further by at least one of acid treatment and pickling.

15. The process according to claim 1, wherein the pulverulent alloy is applied to the support material by spraying.

16. The process according to claim 1, wherein the pulverulent alloy is applied from a liquid suspension by spraying.

17. The process according to claim 1, wherein the catalyst is conditioned by ammonia before the hydrogenation.

18. The process according to claim 1, comprising further modifying the catalyst activated in 3), by application of at least one of metals, metal salts, acids and bases, and optionally by treatment in a reducing or oxidizing atmosphere.

19. The process according to claim 1, wherein the process is carried out batchwise or continuously in one or more stages.

20. The process according to claim 1, wherein the hydrogenation is carried out continuously in a fixed-bed reactor which is operated in the downflow mode or upflow mode.

21. The process according to claim 1, wherein the hydrogenation is carried out at temperatures in the range from 20 to 150° C., and pressures of from 0.3 to 50 MPa.

22. The process according to claim 1, wherein the shaped body obtained in 1) is dried and calcinated.

23. The process according to claim 1, wherein the alloy is a cobalt/nickel/aluminum alloy.

24. The process according to claim 1, wherein the hydrogenation is carried out at temperatures in the range of from 40 to 130° C., and pressures of from 5 to 30 MPa.

* * * * *